United States Patent [19]

Muhammad et al.

[11] Patent Number: 5,167,964

[45] Date of Patent: Dec. 1, 1992

[54] SEMI-ENTERIC DRUG DELIVERY SYSTEMS AND METHODS FOR PREPARING SAME

[75] Inventors: Nouman Muhammad, Long Valley; Michael Harris, Hackettstown; Jay Weiss, East Brunswick; Russell U. Nesbitt, Somerville, all of N.J.

[73] Assignee: Warner-Lambert Company, Morris Plains, N.J.

[21] Appl. No.: 835,798

[22] Filed: Feb. 14, 1992

[51] Int. Cl.⁵ ............................ A61K 9/32; A61K 9/58
[52] U.S. Cl. .............................. 424/482; 424/78.24; 424/472; 424/440; 424/441; 424/480; 424/494; 424/495; 424/497
[58] Field of Search ............... 424/472, 440, 441, 482, 424/480, 78.24, 494, 495, 497; 514/789

[56] References Cited

U.S. PATENT DOCUMENTS

| | | | |
|---|---|---|---|
| 4,263,273 | 4/1981 | Appelgren et al. | 424/497 |
| 4,644,031 | 2/1987 | Lehmann et al. | 424/497 |
| 4,800,079 | 1/1989 | Boyer | 424/482 |
| 4,828,840 | 5/1989 | Sakamoto et al. | 424/472 |

Primary Examiner—Thurman K. Page
Assistant Examiner—Amy Hulina
Attorney, Agent, or Firm—Richard S. Bullitt

[57] ABSTRACT

The present invention pertains to semi-enteric drug delivery systems which comprise (a) an inert core, (b) a first coating layer over the core comprising a medicament, and (c) a second coating layer over the first coating layer comprising a mixture of methacrylic acid copolymer, type C, and povidone present in a ratio by weight of from about 2:1 to about 24:1, respectively.

21 Claims, 4 Drawing Sheets

SEMI-ENTERIC DRUG DELIVERY SYSTEMS AND METHODS FOR PREPARING SAME

BACKGROUND OF THE INVENTION

1. Field of the Invention

This invention pertains to a novel semi-enteric drug delivery systems which comprise an inert core, a first coating layer comprising a medicament, and a second coating layer comprising a mixture of methacrylic acid copolymer, type C, and povidone. Therapeutically effective amounts of the novel semi-enteric drug delivery systems may be utilized in a wide variety of pharmaceutically acceptable carriers and confectionery bulking agents to prepare medicated compositions. This invention also relates to methods for preparing and using these novel semi-enteric drug delivery systems and the medicated compositions in which they may be used.

2. Description of the Background

Enteric coated compositions for the delayed release of medicaments, the protection of acid-labile medicaments, or the encapsulation of irritating medicaments are well known in the art. Enteric coatings are applied to medicaments to prevent release and absorption until the medicament reaches the intestines. Enteric coating materials are generally anionic polymers which are insoluble in buffer solutions below about pH 5 and in gastric fluid but soluble in neutral to weakly alkaline buffer solutions above about pH 5.5 and in intestinal fluid. Release of the medicament within the enteric coating may occur by dissolution, leaching, erosion, rupture, diffusion, or similar actions, depending upon such factors as the nature and thickness of the coating material.

Because enteric coated compositions release no medicament in the stomach and rapidly release the medicament in the intestines, a frequently encountered problem is that such compositions provide only delayed release and not sustained release. This problem is particularly acute when constant blood levels of a medicament must be maintained such as when the medicament is an antibacterial.

U.S. Pat. No. 4,828,840, issued to Sakamoto, discloses a sustained release formulation which comprises an inert core, a powder-coating of an active ingredient, a powder-coating of a water-repellant ingredient, and a film-coating of a pH independent and water-insoluble material. The pH independent and water-insoluble film-coating material may be trimethylammoniummethyl chloride methacrylate (Eudragit ® RS) or polyvinylpyrrolidone.

U.S. Pat. No. 4,263,273, issued to Appelgren et al., discloses an enteric pharmaceutical preparation which comprises an inert core, a first coating layer of a cardiac glycoside, and a second coating layer of an anionic carboxylic polymer insoluble below pH 7.5. The first layer may further comprise a water-soluble polymer such as polyvinylpyrrolidone and the anionic carboxylic polymer may be a partly methyl esterified methacrylic acid polymer such as Eudragit ® L.

U.S. Pat. No. 4,800,079, issued to Boyer, discloses a pharmaceutical preparation which comprises an inert core, a first coating layer of fenofibrate incorporated into the pores of a matrix, and a second protective coating layer. The matrix and second protective coating layer are comprised of a material selected from a group which includes acid-soluble methacrylic acid polymer and polyvinylpyrrolidone.

U.S. Pat. No. 4,520,172, issued to Lehmann et al., discloses an enteric emulsion polymer comprising (a) an alkyl acrylate or alkyl methacrylate, (b) a vinyl or vinylidene monomer having an amino or carboxylic group capable of salt formation, and (c) a vinyl or vinylidene monomer copolymerizable with the components in (a) or (b). The vinyl or vinylidene monomer may be vinylpyrrolidone. U.S. Pat. No. 4,644,031, issued to Lehmann et al., discloses an enteric pharmaceutical dosage form comprising an enteric polymer containing carboxylic groups and a water-insoluble film forming polymer. The enteric polymer and water-insoluble film forming polymer may be an acrylic acid and methacrylic acid copolymer which may also contain vinylpyrrolidone monomer. U.S. Pat. No. 4,705,695, issued to Lehmann et al., discloses an enteric coating comprising a polymer prepared from acrylic acid or methacrylic acid monomers containing a tertiary amine group. The enteric coating may also contain polyvinylpyrrolidone.

While the above references disclose a number of enteric coated compositions, none of the above references disclose semi-enteric compositions Enteric coated compositions provide only delayed release and do not provide sustained release. Thus it would be advantageous to prepare a semi-enteric drug delivery system which would partially release medicament in the stomach for immediate release and thereafter release additional medicament in the intestines for delayed release. The present invention provides such semi-enteric drug delivery systems which are useful to maintain constant blood levels of a medicament. The present invention also provides methods for preparing these novel semi-enteric drug delivery systems and the medicated compositions in which they may be used.

SUMMARY OF THE INVENTION

The present invention pertains to semi-enteric drug delivery systems which comprise (a) an inert core, (b) a first coating layer over the core comprising a medicament, and (c) a second coating layer over the first coating layer comprising a mixture of methacrylic acid copolymer, type C, and povidone present in a ratio by weight of from about 2:1 to about 24:1, respectively. The drug delivery systems may be utilized in a wide variety of pharmaceutically acceptable carriers and confectionery bulking agents to prepare medicated compositions. This invention also relates to methods for preparing these semi-enteric drug delivery systems and the medicated compositions in which they may be employed.

DETAILED DESCRIPTION OF THE INVENTION

Applicants have discovered that the enteric release properties of methacrylic acid copolymer, type C, may be modified by the addition of povidone within a narrow concentration range. Methacrylic acid copolymer, type C, is an anionic polymer normally employed to prepare fully enteric formulations. Medicaments coated with methacrylic acid copolymer, type C, are not released under the pH conditions of the stomach, about 1.2, but are released at a first order release rate under the pH conditions of the intestines, about 5.5. Applicants have found that medicaments coated with mixtures of methacrylic acid copolymer, type C, and povidone according to the present invention show zero order release (constant release) for about two hours in the stomach and continue to show zero order release in the upper part of the intestines. In the lower part of the intestines where the pH is about 7.4, medicaments coated with mixtures of methacrylic acid copolymer, type C, and povidone according to the present invention show first order release. Hence, by carefully controlling the concentration of methacrylic acid copolymer, type C, and povidone in a coating layer, semi-enteric drug delivery systems can be prepared to provide a controlled and sustained release of medicament in the stomach and the upper parts of the small intestine.

The semi-enteric drug delivery systems of the present invention comprise (a) an inert core, (b) a first coating layer over the core comprising a medicament, and (c) a second coating layer over the first coating layer comprising a mixture of methacrylic acid copolymer, type C, and povidone present in a ratio by weight of from about 2:1 to about 24:1, respectively.

The inert core in the semi-enteric drug delivery system of the present invention may be any core material which is pharmacologically inert and does not interact with the medicament. Nonlimiting examples of inert cores useful in the present invention include saccharides and sugar alcohols such as sucrose, lactose, mannitol, xylitol, and the like, as well as celluloses and starches. The inert cores may be employed in the form of crystals, granules, tablets, or beads. The amount of inert core present in the semi-enteric drug delivery system will be an effective amount to support the medicament. In general, the inert core will be present in the semi-enteric drug delivery system in amount from about 20% to about 50%, preferably from about 25% to about 40%, and more preferably from about 25% to about 35%, by weight.

The medicaments (drugs, pharmaceuticals) present in the first coating layer of the semi-enteric drug delivery system may be selected from a wide variety of water-soluble and water-insoluble drugs and their acid addition salts. Both organic and inorganic salts may be used provided the drug maintains its therapeutic effect. Exemplary acid salts include hydrochloride, hydrobromide, orthophosphate, benzoate, maleate, tartrate, succinate, citrate, salicylate, sulfate, and acetate.

The medicament may be selected from a wide range of therapeutic agents and mixtures of therapeutic agents which may be administered in semi-enteric form. Nonlimiting illustrative categories and specific examples of such medicaments include:

(a) Analgesics, such as acetylsalicylic acid, acetaminophen, ibuprofen, phenacetin, phenylbutazone, salicylamide, and sodium salicylate;

(b) Anthelmintics, such as dithiazanine iodide and gardona;

(c) Antiasmatics, such as aminophylline, metaproterenol, epinephrine, and theophylline;

(d) Antibacterials, such as doxycycline hyclate (doxycycline hydrochloride), minocycline hydrochloride, oxytetracycline hydrochloride, chlortetracycline hydrochloride, and demeclocycline hydrochloride;

(e) Anticholesterolemic and antilipid agents, such as gemfibrozil;

(f) Antiemetics, such as prochloroperazine dimaleate;

(g) Antihistamines, such as chlorpheniramine maleate, brompheniramine maleate, phenindamine tartrate, pyrilamine maleate, methapyrilene fumarate, doxylamine succinate, phenyltoloxamine citrate, diphenylhydramine hydrochloride, promethazine, terfenedine, and triprolidine;

(h) Anti-inflammatory agents, such as isoxicam, meclophenamic acid, and naproxen;

(i) Antinauseants, such as dimenhydrinate and meclizine;

(j) Antipyretics, such as N-acetyl-p-aminophenol;

(k) Antitussives, such as dextromethorphan, dextromethorphan hydrobromide, noscapine, carbetapentane citrate, chlophedianol hydrochloride, codeine, and diphenhydramine hydrochloride;

(l) Appetite suppressants, such as phenylpropanolamine hydrochloride and caffeine;

(m) Cathartics, such as castor oil;

(n) Central nervous system stimulants, such as nicotine and caffeine;

(o) Decongestants, such as phenylephrine hydrochloride, phenylpropanolamine hydrochloride, pseudoephedrine hydrochloride, pseudoephedrine hydrobromide, pseudoephedrine sulfate, and ephedrine;

(p) Expectorants, such as guaifenesin, glycerol, and guaiacolate;

(q) Laxatives, such as phenolphthalein, danthron, pamabrom, and bisocadyl;

(r) Nutritional supplements, including vitamins and minerals, such as niacin, pantothenic acid, vitamin B6, thiamine hydrochloride, riboflavin, potassium iodide, potassium chloride, cupric sulfate, and ferrous sulfate; and (s) Various alkaloids, such as codeine phosphate, codeine sulfate, and morphine.

In a preferred embodiment, the medicament is a water-soluble antibacterial selected from the group consisting of doxycycline hyclate, minocycline hydrochloride, oxytetracycline hydrochloride, chlortetracycline hydrochloride, demeclocycline hydrochloride, and mixtures thereof. In a more preferred embodiment the medicament is doxycycline hyclate.

The medicament of the present invention may be used in many distinct physical forms well known in the pharmaceutical art to provide an initial dosage of the medicament, a further time-release form of the medicament, or both. Without being limited thereto, such physical forms include free forms, encapsulated forms, and mixtures thereof.

The amount of medicament drug used in the present invention is an effective amount which may vary depending upon the therapeutic dosage recommended or permitted for the particular medicament. In general, the amount of medicament present is the ordinary dosage required to obtain the desired result. Such dosages are known to the skilled practitioner in the medical arts and are not a part of the present invention. In general, the first coating layer will be present in the semi-enteric drug delivery system in an amount from about 37% to about 75%, preferably from about 45% to about 70%, and more preferably from about 55% to about 65%, by weight.

The second coating layer of the semi-enteric drug delivery system comprises a mixture of methacrylic acid copolymer, type C, and povidone. Methacrylic acid copolymer (USP/NF) is a fully polymerizable anionic copolymer of methacrylic acid and an acrylic or methacrylic ester. Several types of methacrylic acid copolymer are available depending upon the assay and viscosity requirements Methacrylic acid copolymer, type C, has from 46% to 50.6% methacrylic acid units, on a dried basis, and a viscosity from 100cps to 200cps. Films formed from methacrylic acid copolymer, type C, are insoluble in acid solution and soluble in neutral and weakly alkaline solutions. Methacrylic acid copolymer, type C, is commercially available under the tradename Eudragit® L30D through Rohm Pharma, GMBH, Weiterstadt as an aqueous dispersion of an anionic copolymer based on methacrylic acid and ethyl acrylate.

Povidone (USP/NF, 1-ethenyl-2-pyrrolidone polymers, polyvinylpyrrolidone, PVP) is a free flowing amorphous powder soluble in water and organic solvents. Povidine is a synthetic polymer consisting of linear 1-vinyl-2-pyrrolidone groups. The degree of polymerization results in polymers of various molecular weights ranging from about 10,000 to about 700,000. Povidine may be represented by the formula:

The amount by weight of povidone added to methacrylic acid copolymer, type C, in the second coating layer is an effective amount to prepare a semi-enteric formulation. An effective amount of povidone is an amount which will modify the enteric release properties of methacrylic acid copolymer, type C, and thereby provide to a medicament coated with a mixture of povidone and methacrylic acid copolymer, type C, zero order release in the stomach and in the upper part of the intestines. The exact ratio by weight of methacrylic acid copolymer, type C, to povidone is a matter of preference, subject to such factors as the type of medicament employed, the exact type of methacrylic acid copolymer, type C, and povidone employed, and the other ingredients in the semi-enteric drug delivery system. Thus, the ratio by weight of methacrylic acid copolymer, type C, to povidone may be varied in order to obtain the result desired in the final product. In general, the ratio by weight of methacrylic acid copolymer, type C, to povidone in the second coating layer of the semi-enteric drug delivery system will be from about 2:1 to about 24:1, preferably from about 4:1 to about 8:1, and more preferably from about 5:1 to about 7:1, respectively.

The amount of second coating layer used in the drug delivery system of the present invention is an effective amount to provide semi-enteric release. The exact amount of second coating layer is a matter of preference subject to such factors as the particular release properties desired and the medicament employed In general, the second coating layer will be present in the semi-enteric drug delivery system in an amount from about 5% to about 30%, preferably from about 6% to about 15%, and more preferably from about 8% to about 12%.

In another embodiment, the first coating layer in the semi-enteric drug delivery system may further comprise a gliding agent. Gliding agents (glidants) are compounds which have particles that readily slide over one another to produce an antifriction or lubricating effect. Suitable gliding agents in the present invention include colloidal silicon dioxide, talc, and the like, and mixtures thereof. Preferably, the gliding agent is colloidal silicon dioxide. The gliding agent, when present in the first coating layer, will be present in an amount up to about 1%, and preferably about 0.01%, by weight.

In another embodiment, the first coating layer in the semi-enteric drug delivery system may further comprise a binding agent. Binding agents (binders) are compounds which exert a strong physiochemical attractive force between molecules. Suitable binding agents in the present invention include cellulose derivatives such as ethylcellulose, hydroxypropyl-cellulose, hydroxypropyl-methylcellulose, hydroxypropyl-methylcellulose phthalate, methylcellulose, sodium carboxymethylcellulose, and the like, and mixtures thereof. Preferably, the binding agent is hydroxypropylcellulose. The binding agent, when present in the first coating layer, will be present in an amount from about 1% to about 4%, and preferably about 2%, by weight.

In another embodiment, the second coating layer in the semi-enteric drug delivery system may further comprise a plasticizing agent. Plasticizing agents (plasticizers) are organic molecules added to polymers to facilitate processing by increasing the flexibility and toughness of the final product by internally modifying (solvating) the polymer molecule. Plasticizing agents should be soluble in the polymer they are designed to plasticize, should not be highly water-soluble, and should be safe for the intended use. Suitable plasticizing agents in the present invention are nonvolatile organic liquids and low melting solids, such as esters of phthalic acid, adipic acid, and sebacic acid, and polyols such as ethylene glycol and its derivatives, tricresyl phosphate, castor oil, and the like, and mixtures thereof. Other suitable partly water-soluble to water-insoluble plasticizing agents that may be employed are dibutyl sebacate triethyl citrate, tributyl citrate, triacetin, and acetylated mono-, di- and triglycerides, and the like, and mixtures thereof. Other suitable plasticizing agents include acetyltriethylcitrate, triethyl citrate, acetyltributylcitrate, tributylcitrate, and the like, and mixtures thereof. Preferably, the plasticizing agent is triethyl citrate. The plasticizing agent, when present in the second coating layer, will be present in an amount up to about 3%, and preferably about 0.7%, by weight.

In another embodiment, the second coating layer in the semi-enteric drug delivery system may further comprise an anti-adhering agent. Anti-adhering agents (anti-adherents, dispersing agents) are surface-active agents which may be added to a suspension to promote uniform separation of extremely fine (colloidal) solid particles. Suitable anti-adhering agents in the present invention include polymeric electrolytes, condensed silicates, polyphosphates, lignin derivatives including aluminum stearate, aluminum laurate, magnesium stearate, calcium stearate, zinc stearate, talc, kaolin, fumed silica, and the like, and mixtures thereof. Preferably, the anti-adhering agent is kaolin. The anti-adhering agent, when present in the second coating layer, will be present in an amount up to about 2%, and preferably about 1.2%, by weight.

The present invention also extends to methods for preparing the semi-enteric drug delivery systems. In such a method, the medicament, preferably mixed with a gliding agent, is powder layered, preferably with the aid of a binding agent, onto inert cores to form coated cores. The inert cores may be powder coated using standard techniques and equipment known to those skilled in the art. The coated inert cores are then spray coated with the second coating layer in a fluid bed dryer by suspending the coated cores in a stream of air or strong upward air current and passing the stream through a zone of finely atomized droplets of the coating layer mixture (encapsulant), after which the coated particles pass out of the upward stream and pass downward in a fluidized condition countercurrent to a flow of heated fluidized gas whereupon they are dried, and may re-enter the upward-moving coating zone for a subsequent discreet coating application. The coated cores of the present invention may be spray coated using standard techniques and equipment known to those skilled in the art. The exact conditions for spray coating will vary with the particular fluid bed apparatus selected and are readily determined by those skilled in the art without the need for undue experimentation. Fluid bed apparatus is well known in the arts and therefore the selection of the specific apparatus will be apparent to the artisan In one embodiment, the method and apparatus employed is known as the Wurster Process. The Wurster Process and its associated apparatus are disclosed in detail, for example, in U.S. Pat. Nos. 3,089,824, 3,117,027, 3,196,827, 3,241,520, and 3,253,944, which disclosures are incorporated herein by reference. In a preferred embodiment, the apparatus is a Versa-Glatt model GPCG 1 fluidized bed apparatus with a Wurster column.

In a specific embodiment, the present invention is directed to a method for preparing a semi-enteric drug delivery system which comprises the steps of:
(A) providing the following ingredients:
  (a) an inert core;
  (b) a first coating layer over the core comprising a medicament; and
  (c) a second coating layer over the first coating layer comprising a mixture of methacrylic acid copolymer, type C, and povidone present in a ratio by weight of from about 2:1 to about 24:1, respectively;
(B) powder layering the inert core with the first coating layer; and
(C) spray coating the coated core of step (B) with the second coating layer to form the semi-enteric drug delivery system.

Once prepared, the semi-enteric drug delivery systems may be stored for future use or may be formulated with conventional additives such as pharmaceutically acceptable carriers and confectionery bulking agents to prepare a wide variety of medicated compositions to suit particular applications.

An important aspect of the present invention includes a hard or soft confectionery composition incorporating the inventive semi-enteric drug delivery systems and a method for preparing the hard or soft confections. In this form of the invention, the confectionery composition includes a pharmaceutically acceptable carrier such as a confectionery bulking agent, the inventive semi-enteric drug delivery system, and various additives. The confectionery may be in the form of a lozenge, tablet, toffee, nougat, suspension, chewy candy, and the like. The pharmaceutically acceptable carriers may be prepared from a wide range of materials. Without being limited thereto, such materials include diluents, binders and adhesives, lubricants, disintegrants, coloring agents, bulking agents, flavoring agents, sweetening agents and miscellaneous materials such as buffers and adsorbents in order to prepare a particular medicated confection.

The preparation of confectionery formulations is historically well known and has changed little through the years. Confectionery items have been classified as either "hard" confectionery or "soft" confectionery. The semi-enteric drug delivery systems of the present invention may be incorporated into confectionery compositions by admixing the inventive drug delivery systems into conventional hard and soft confections.

As used herein, the term confectionery material means a product containing a bulking agent selected from a wide variety of materials such as sugar, corn syrup, and the like, and in the case of sugarless bulking agents, sugar alcohols such as sorbitol, mannitol, and the like, and mixtures thereof. Confectionery material may include such exemplary substances as lozenges, tablets, toffee, nougat, suspensions, chewy candy, chewing gum and the like. The bulking agent is present in a quantity sufficient to bring the total amount of confectionery composition to 100%.

Lozenges are flavored medicated dosage forms intended to be sucked and held in the mouth. Lozenges may be in the form of various shapes such as flat, circular, octagonal, and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition.

The syrup component is generally prepared from corn syrups high in fructose, but may include other materials. Further ingredients such as flavoring agents, sweetening agents, acidulants, coloring agents, and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and the cooking continued until a final temperature of 145° C. to 156° C. is achieved. The batch is then cooled and worked as a plastic-like mass to incorporate additives such as flavoring agents, coloring agents and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and Worked as a plastic-like mass enabling incorporation of the additives, such as flavor agents, coloring agents and the like.

In vacuum cookers, the carbohydrate bulking agent is boiled at a temperature from about 125° C. to about 132° C., vacuum is applied and additional water is boiled off without extra heating. When cooking is complete, the mass is a semi-solid and has a plastic-like consistency. At this point, flavoring agents, coloring agents, and other additives are admixed in the mass by routine mechanical mixing operations.

The optimum mixing required to uniformly mix the flavoring agents, coloring agents, and other additives during conventional manufacturing of boiled candy lozenges is determined by the time needed to obtain a uniform distribution of the materials. Normally, mixing times of from about 4 to about 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets*, Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents, and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agents, coloring agents, preservatives, medicaments, mixtures thereof and the like may be added thereafter also under agitation. A general discussion of the composition and preparation of nougat confections may be found in B. W. Minifie, *Chocolate, Cocoa and Confectionery*: Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 1100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes The novel semi-enteric drug delivery systems may also be in the form of a pharmaceutical suspensions. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as benzoic acid, sorbic acid, methyl paraben, and propyl paraben. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate which may be present in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose which may be present in amounts up to about 20%, and preferably from about 1% to about 15%, by weight of the suspension;

(d) antifoaming agents such as dimethyl polysiloxane which may be present in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents ma also include natural food colors and dyes suitable for food, drug and cosmetic applications. These coloring agents are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) vehicles such as alcohol, propylene glycol, polyethylene glycol, edible oils such as animal, vegetable and mineral oils, and the like may be used to solubilize the flavoring agents. In general, vehicles may be used in amounts up to about 10%, and preferably from about 2% to about 5%, by weight of the suspension.

The pharmaceutical suspensions of the present invention may be prepared as follows:

(A) admix the thickener with the vehicle heated to a temperature from about 40° C. to about 95° C., preferably from about 40° C. to about 70° C., to form a dispersion if the thickener is soluble in the vehicle or a solution if the thickener is soluble in the soluble;

(B) admix the sweetening agent with the vehicle to form a solution;

(C) admix the semi-enteric drug delivery system composition with the thickener-vehicle admixture to form a uniform thickener-sustained release composition;

(D) combine the sweetener solution with the thickener-sustained release composition and mix until uniform; and (E) admix the optional adjunct materials such as coloring agents, flavoring agents, decolorants, solubilizing agents, antifoaming agents, buffers and additional vehicle with the mixture of step (D) to form the suspension.

To achieve acceptable stability and quality as well as good taste and mouth feel in a sustained release formulation several considerations are important. These considerations include the amount of active substance per tablet, the flavoring agent employed, the degree of compressibility of the tablet and the organoleptic properties of the pharmaceutical composition.

Medicated candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The semi-enteric drug delivery systems of the instant invention can then be added to the homogeneous mixture as the temperature is lowered to about 65° C.-95° C. whereupon additional ingredients can then be added such as flavoring agents and coloring agents. The formulation is further cooled and formed into pieces of desired dimensions.

A general discussion of the lozenge and tablet forms of confectionery may be found in H. A. Lieberman and L. Lachman, *Pharmaceutical Dosage Forms: Tablets* Volume 1, Marcel Dekker, Inc., New York, N.Y. at pages 289 to 466, which disclosure is incorporated herein by reference.

In accordance with this invention, therapeutically effective amounts of the semi-enteric drug delivery systems of the present invention may be admixed into the hard and soft confections. These amounts are readily determined by those skilled in the art without the need for undue experimentation. The exact amount of the semi-enteric drug delivery system employed in the hard and soft confections will vary with the particular medicament selected. In a preferred embodiment, the semi-enteric drug delivery systems are present in the hard and soft confection compositions in percentages by weight in an amount from about 5% to about 50%, more preferably from about 110% to about 40%, and most preferably, in an amount from about 10% to about 30%. The pharmaceutically acceptable carrier and optional additives are present in a quantity sufficient to bring the total amount of hard and soft confection composition to 100%.

The present invention extends to methods for making the improved medicated hard and soft confection compositions. The semi-enteric drug delivery systems may be incorporated into otherwise conventional hard or soft confections to prepare medicated compositions using standard techniques and equipment known to those skilled in the art. The apparatus useful in accordance with the present invention comprises cooking and mixing apparatus well known in the confectionery manufacturing arts, and therefore the selection of the specific apparatus will be apparent to the artisan.

In a specific embodiment, the present invention is directed at a medicated composition which comprises a pharmaceutically acceptable carrier and a therapeutically effective amount of a semi-enteric drug delivery system, wherein the drug delivery system comprises:

(a) an inert core;

(b) a first coating layer over the core comprising a medicament; and (c) a second coating layer over the first coating layer comprising a mixture of methacrylic acid copolymer, type C, and povidone present in a ratio by weight of from about 2:1 to about 24: , respectively.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES 1-4

These Examples demonstrate the preparation of semi-enteric drug delivery systems according to the present invention.

Coated core particles were prepared by the powder layering technique having the composition set out in Table 1.

TABLE 1

| Semi-Enteric Drug Delivery System Coated Cores | | |
|---|---|---|
| Ingredient | Amount | % By weight of the total Drug Delivery System |
| Doxycycline Hyclate | 1000 g | 59 |
| Colloidal silicon dioxide | 1 g | 0.1 |
| Sugar spheres | 500 g | 30 |
| 8% Hydroxypropyl Cellulose solution | 33 g | 2 |

The coated core particles were prepared by first passing doxycycline hyclate through a Fitzmill N000 screen and colloidal silicon dioxide through a no. 100 screen. The screened doxycycline hyclate and colloidal silicon dioxide were then blended and powder layered onto sugar spheres (mesh size 20-25) using a CF Granulator (CF 360) and 8% hydroxypropyl cellulose solution as a binding agent. The conditions for powder layering the cores were the following: 1.0 bar atomization; rotar, 160 rpm; powder delivery rate, 10 rpm; spray rate, 8ml/min; and product temperature, 24° C. The powder layered cores were then dried overnight in an oven at 45° C. to yield 1534g of doxycycline hyclate powder layered cores.

The powder layered core particles were then spray coated with the second coating layer having the composition set out in Table 2.

TABLE 2

| Semi-Enteric Drug Delivery System Second Coating Layer | | |
|---|---|---|
| Ingredient | Amount | % By weight of the total Second Coating Layer |
| Eudragit ® L30D (30% wt/wt) | 133.8 g | 28% |
| Povidone | 3.3 g | 1.36% |
| Triethyl citrate | 4.3 g | 0.9% |
| Kaolin | 7.9 g | 1.65 % |
| Water | 328.5 g | q.s. to 100% |

The second coating layer was prepared by first dissolving povidone in water, then adding kaolin to the solution, and mixing the solution for 20 minutes. Triethyl citrate was then added to the solution and the mixing Was continued for 15 minutes. Eudragit ® L30D was then added to the solution and the resulting suspension was mixed for 30 minutes, then passed through a no. 40 screen.

The second coating layer suspension was then spray coated onto 500g of doxycycline hyclate powder layered cores using a Glatt GPCG3 machine until a 10% weight increase was realized. The twice coated cores were dried in the spray coating machine for 45 minutes at an inlet temperature of 45° C. and a product temperature of 34° C. to yield 550g of the doxycycline hyclate semi-enteric drug delivery system. The doxycycline hyclate drug delivery system contained a second coating layer comprising 68.2% methacrylic acid copolymer, type C, and 11% povidone, by weight of the second coating layer, (Example 1).

For comparison purposes, doxycycline hyclate drug delivery systems were prepared according to the method set out above containing second coating layers having varying amounts of methacrylic acid copolymer, type C, and povidone. The second coating layers (10% coating level) comprised 76.9% methacrylic acid copolymer, type C, (Example 2), 74.5% methacrylic acid copolymer, type C, and 3% povidone (Example 3), and 63.1% methacrylic acid copolymer, type C, and 18% povidone (Example 4), by weight of the second coating layer.

Figure 1:
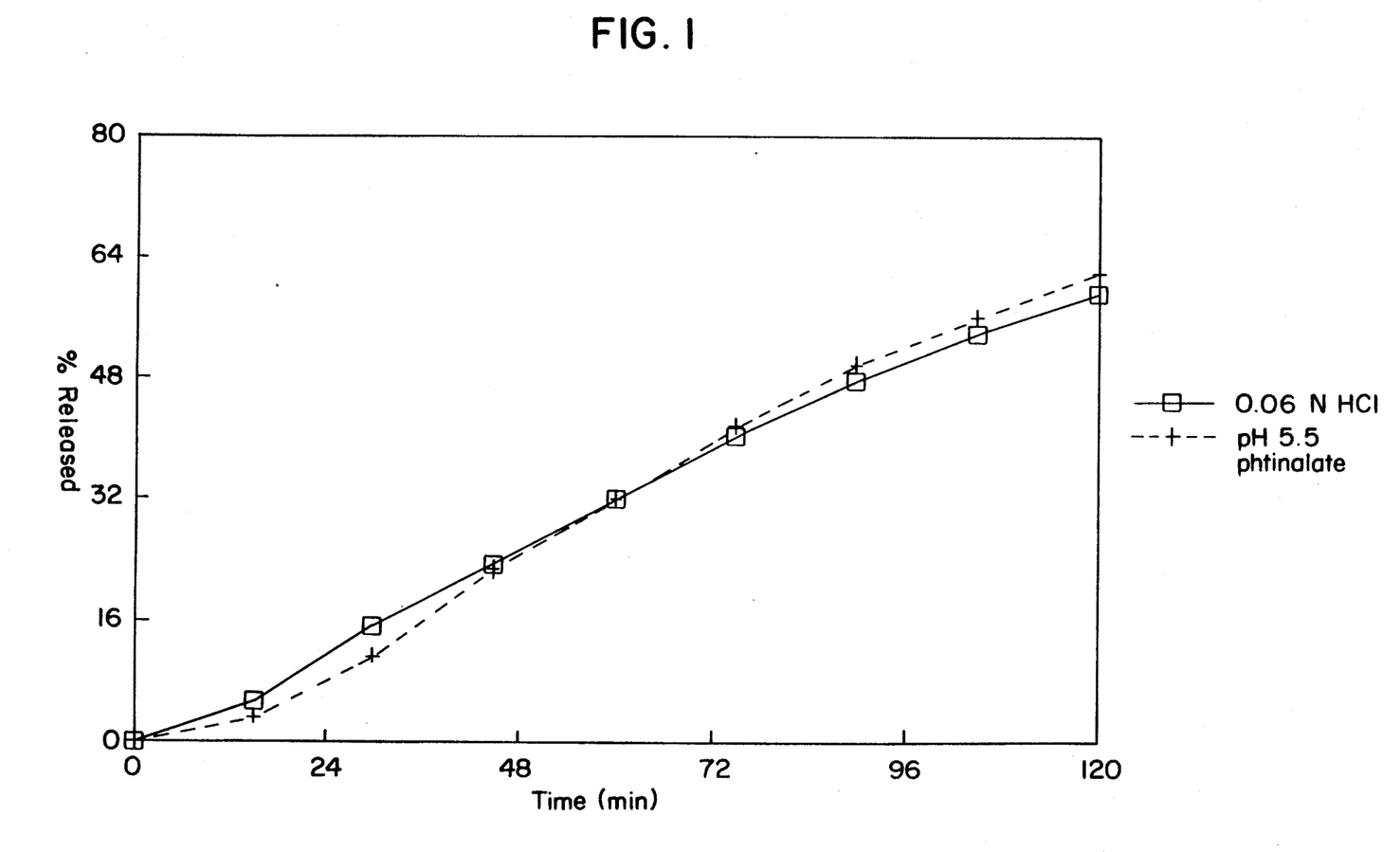
FIG. 1 is a graph illustrating the zero order release of doxycycline hyclate from a semi-enteric drug delivery system at pH 1.2 (0.06N HCl, stomach) and at pH 5.5 (phthalate buffer, upper intestine). The semi-enteric coating layer comprised 68.2% methacrylic acid copolymer, type C, and 11% povidone (Example 1).
Figure 2:
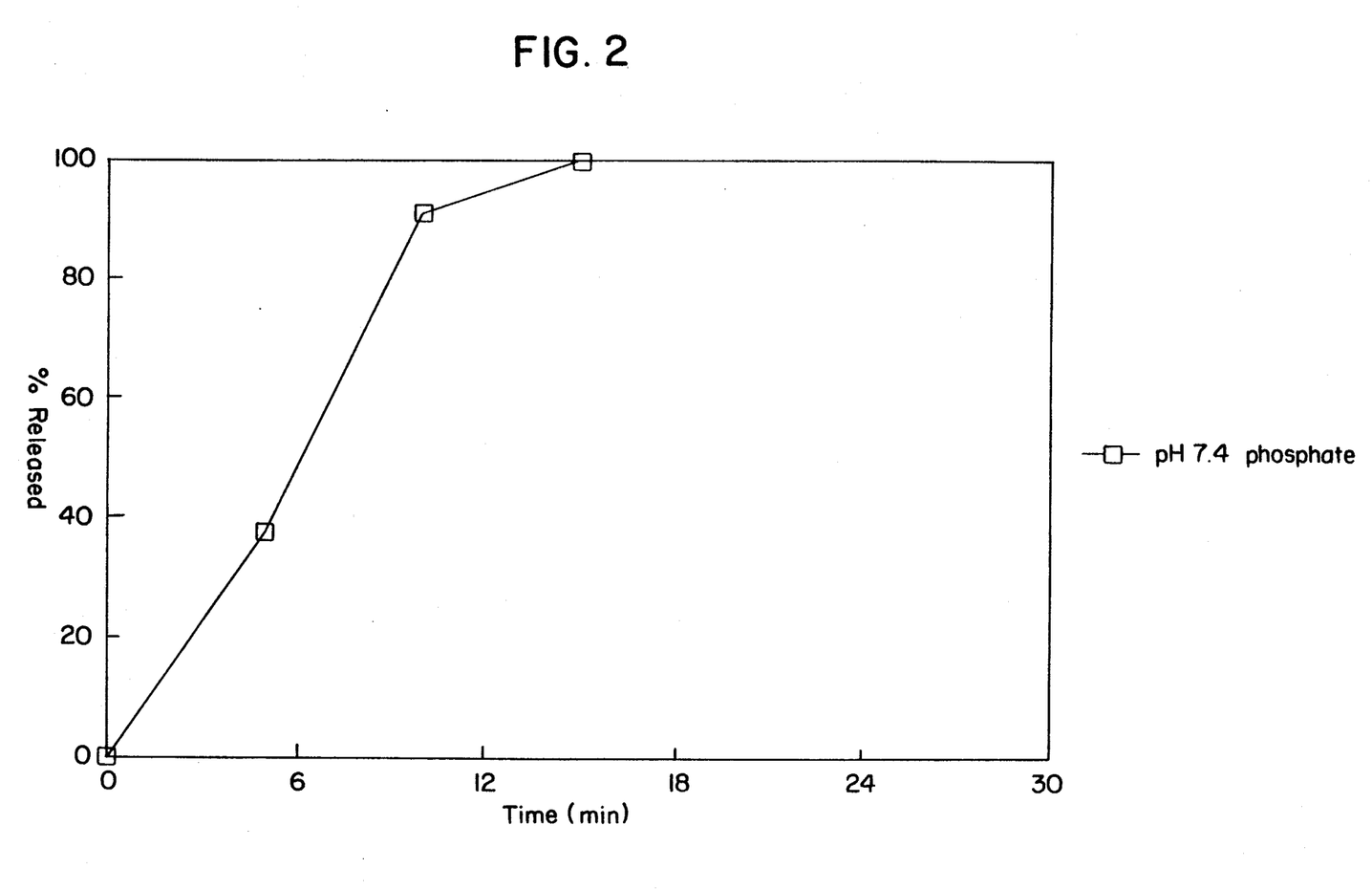
FIG. 2 is a graph illustrating the first order release of doxycycline hyclate from a semi-enteric drug delivery system at pH 7.4 (phosphate buffer, lower intestine). The semi-enteric coating layer comprised 68.2% methacrylic acid copolymer, type C, and 11% povidone (Example 1).

The release of doxycycline hyclate from the drug delivery systems prepared above were then measured at different pH levels. FIG. 1 shows the zero order release of doxycycline hyclate at pH 1.2 (0.06N HCl, stomach) and at pH 5.5 (phthalate buffer, upper intestine) from the semi-enteric drug delivery system of Example 1 wherein the second coating layer comprised 68.2% methacrylic acid copolymer, type C, and 11% povidone, by weight of the second coating layer. FIG. 2 shows the first order release of doxycycline hyclate at pH 7.4 (phosphate buffer, lower intestine) from the semi-enteric drug delivery system of Example 1.

Figure 3:
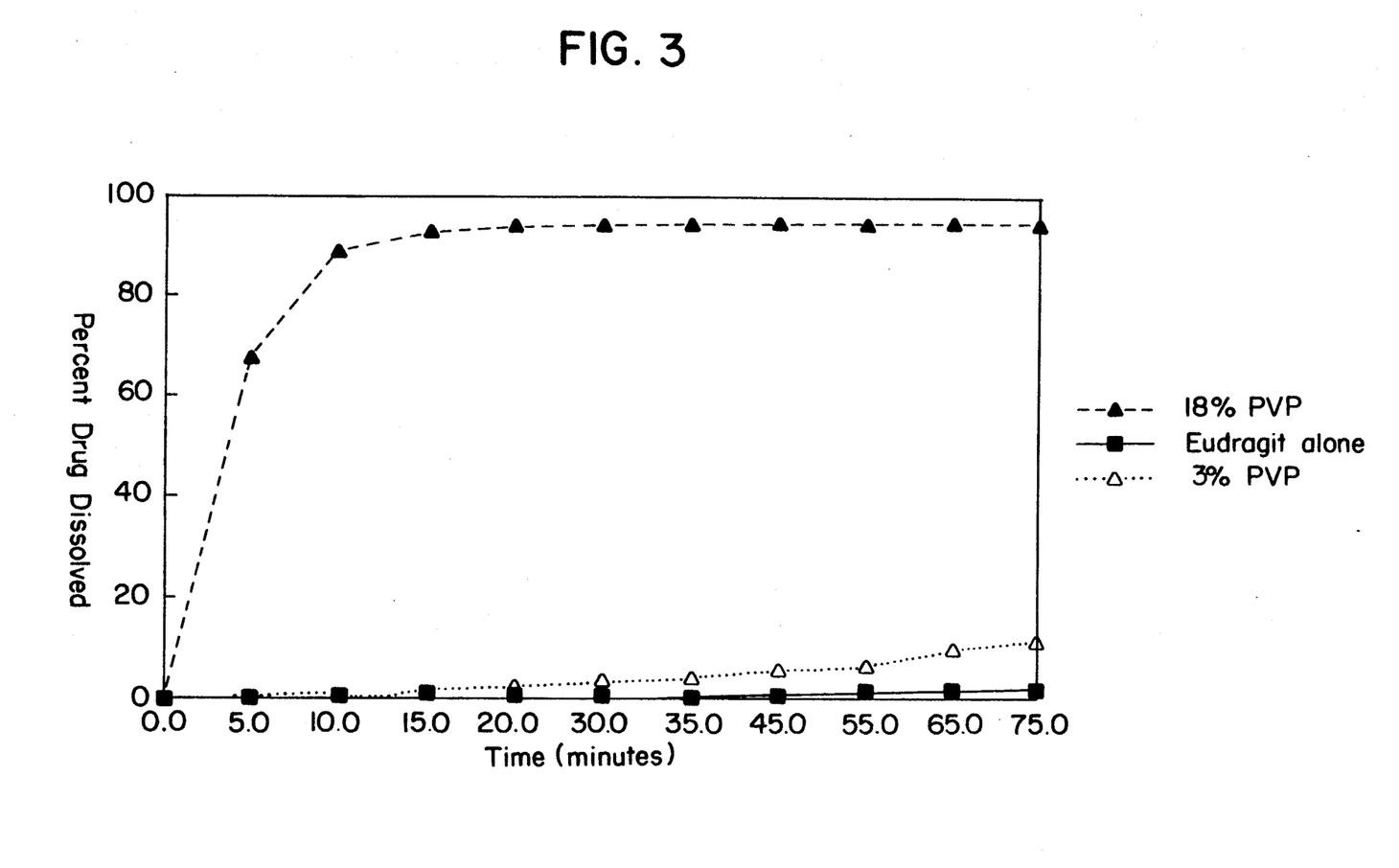
FIG. 3 is a graph illustrating a comparison of the release rates of doxycycline hyclate from three drug delivery systems at pH 1.2 (0.06N HCl, stomach). The coating layers comprised 76.9% methacrylic acid copolymer, type C, (Example 2), 74.5% methacrylic acid copolymer, type C, and 3% povidone (Example 3), and 63.1% methacrylic acid copolymer, type C, and 18% povidone (Example 4).

FIG. 3 shows a comparison of the release rates of doxycycline hyclate from the three drug delivery systems of Examples 2, 3, and 4 at pH 1.2 (0.06N HCl, stomach). The drug delivery system containing 76.9% methacrylic acid copolymer, type C, as the coating layer (Example 2) released essentially no doxycycline hyclate after 75 minutes, the drug delivery system containing 74.5% methacrylic acid copolymer, type C, and 3% povidone as the coating layer (Example 3) released only about 10% of the doxycycline hyclate after 75 minutes, and the drug delivery system containing 63.1% methacrylic acid copolymer, type C, and 18% povidone as the coating layer (Example 4) released over 90% of the doxycycline hyclate after 15 minutes.

Figure 4:
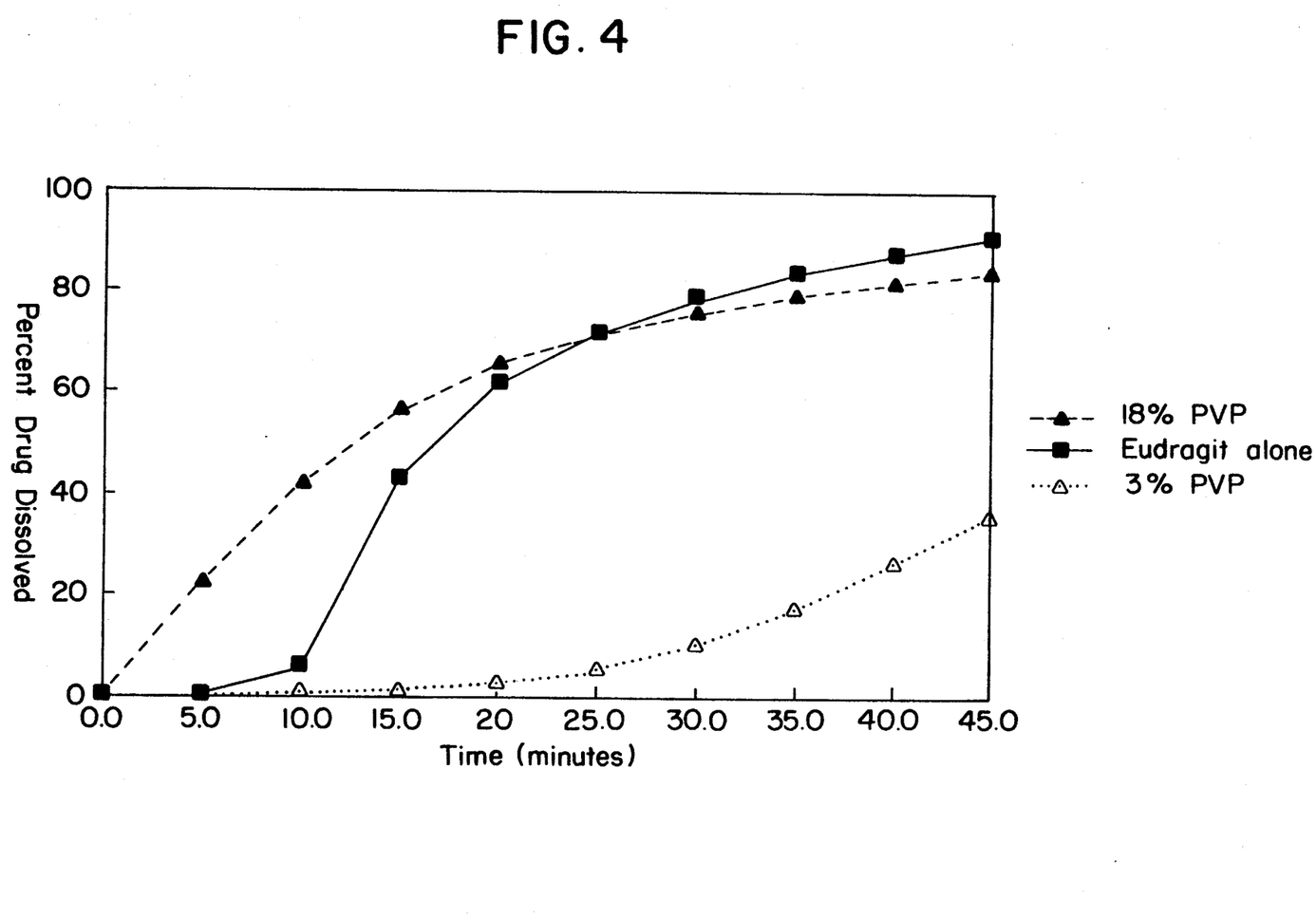
FIG. 4 is a graph illustrating a comparison of the release rates of doxycycline hyclate from three drug delivery systems at pH 5.5 (phthalate buffer, upper intestine). The coating layers comprised 76.9% methacrylic acid copolymer, type C, (Example 2), 74.5% methacrylic acid copolymer, type C, and 3% povidone (Example 3), and 63.1% methacrylic acid copolymer, type C, and 18% povidone (Example 4).

FIG. 4 shows a comparison of the release rates of doxycycline hyclate from the three drug delivery systems of Examples 2, 3, and 4 at pH 5.5 (phthalate buffer, upper intestine). The drug delivery systems containing 76.9% methacrylic acid copolymer, type C, as the coating layer (Example 2) and 74.5% methacrylic acid copolymer, type C, and 3% povidone as the coating layer (Example 3) released over 80% of the doxycycline hyclate after 45 minutes While the drug delivery system containing 63.1% methacrylic acid copolymer, type C, and 18% povidone as the coating layer (Example 4) released less than 40% of the doxycycline hyclate after 45 minutes.

Accordingly, only the drug delivery system of Example 1 provided semi-enteric release of the medicament. The drug delivery systems of Example 2 and 3 provided essentially full enteric release of the medicament while the drug delivery system of Example 4 provided almost no enteric release. These Examples show that the enteric release properties of methacrylic acid copolymer, type C, may be modified by the addition of povidone in a narrow concentration range to prepare semi-enteric formulations.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

We claim:

1. A semi-enteric drug delivery system which comprises:
   (a) an pharmacologically inert core;
   (b) a first coating layer over the core comprising a medicament; and
   (c) a second coating layer over the first coating layer comprising a mixture of an aqueous dispersion of an anionic copolymer based on methacrylic acid and ethylacrylate and povidone present in a ratio by weight of from about 2:1 to about 24:1, respectively.

2. The drug delivery system according to claim 1, wherein the pharmacologically inert core is present in the drug delivery system in an amount from about 20% to about 50%, by weight.

3. The drug delivery system according to claim 1, wherein the medicament in the first coating layer is a water-soluble medicament selected from the group consisting of doxycycline hyclate, minocycline hydrochloride, oxytetracycline hydrochloride, chlortetracycline hydrochloride, and demeclocycline hydrochloride, and mixtures thereof.

4. The drug delivery system according to claim 1, wherein the first coating layer is present in the drug delivery system in an amount from about 37% to about 75%, by weight.

5. The drug delivery system according to claim 1, wherein the mixture of methacrylic acid copolymer, and povidone in the second coating layer is present in a ratio by weight of from about 4:1 to about 8:1, respectively.

6. The drug delivery system according to claim 1, wherein the second coating layer is present in the drug delivery system in an amount from about 5% to about 30%, by weight.

7. The drug delivery system according to claim 1, wherein the first coating layer further comprises a gliding agent present in the drug delivery system in an amount up to about 1%, by weight.

8. The drug delivery system according to claim 1, wherein the first coating layer further comprises a binding agent present in the drug delivery system in an amount from about 1% to about 4%, by weight.

9. The drug delivery system according to claim 1, wherein the second coating layer further comprises a plasticizing agent present in the drug delivery system in an amount up to about 3%, by weight.

10. The drug delivery system according to claim 1, wherein the second coating layer further comprises an anti-adhering agent present in the drug delivery system in an amount up to about 2%, by weight.

11. A method for preparing a semi-enteric drug delivery system which comprises the steps of:
    (A) providing the following ingredients:
       (a) a pharmacologically inert core;
       (b) first coating layer over the core comprising a medicament; and
       (c) a second coating layer over the first coating layer comprising a mixture of an aqueous dispersion of an anionic copolymer based on methacrylic acid and ethylacrylate and povidone present in a ratio by weight of from about 2:1 to about 24:1, respectively;
    (B) powder layering the pharmacologically inert core with the first coating layer; and
    (C) spray coating the coated core of step (B) with the second coating layer to form the semi-enteric drug delivery system.

12. The method according to claim 11, wherein the pharmacologically inert core is present in the drug delivery system in an amount from about 20% to about 50%, by weight.

13. The method according to claim 11, wherein the medicament in the first coating layer is a water-soluble medicament selected from the group consisting of doxycycline hyclate, minocycline hydrochloride, oxytetracycline hydrochloride, chlortetracycline hydrochloride, and demeclocycline hydrochloride, and mixtures thereof.

14. The method according to claim 11, wherein the first coating layer is present in the drug delivery system in an amount from about 37% to about 75%, by weight.

15. The method according to claim 11, wherein the mixture of methacrylic acid copolymer, and povidone in the second coating layer is present in a ratio by weight of from about 4:1 to about 8:1, respectively.

16. The method according to claim 11, wherein the second coating layer is present in the drug delivery system in an amount from about 5% to about 30%, by weight.

17. The method according to claim 11, wherein the first coating layer further comprises a gliding agent present in the drug delivery system in an amount up to about 1%, by weight.

18. The method according to claim 11, wherein the first coating layer further comprises a binding agent present in the drug delivery system in an amount from about 1% to about 4%, by weight.

19. The method according to claim 11, wherein the second coating layer further comprises a plasticizing agent present in the drug delivery system in an amount up to about 3%, by weight.

20. The method according to claim 11, wherein the second coating layer further comprises an anti-adhering agent present in the drug delivery system in an amount up to about 2%, by weight.

21. A medicated composition which comprises a pharmaceutically acceptable carrier and a therapeutically effective amount of a semi-enteric drug delivery system, wherein the drug deliver system comprises:
  (a) a pharmacologically inert core;
  (b) a first coating layer over the core comprising a medicament; and
  (c) a second coating layer over the first coating layer comprising a mixture of an aqueous dispersion of an anionic copolymer based on methacrylic acid and ethylacrylate and povidone present in a ratio by weight of from about 2:1 to about 24:1, respectively.

* * * * *